(12) United States Patent
Park et al.

(10) Patent No.: US 8,034,602 B2
(45) Date of Patent: Oct. 11, 2011

(54) **METHOD FOR PRODUCING L-ARGININE USING *CORYNEBACTERIUM GLUTAMICUM***

(75) Inventors: Young Hoon Park, Gyeonggi-do (KR); Hye Won Kim, Gyeonggi-do (KR); Ji-Hye Lee, Gyeonggi-do (KR); Soo-Youn Hwang, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 369 days.

(21) Appl. No.: 12/309,048

(22) PCT Filed: Jul. 12, 2007

(86) PCT No.: PCT/KR2007/003392
§ 371 (c)(1),
(2), (4) Date: Jan. 5, 2009

(87) PCT Pub. No.: WO2008/007915
PCT Pub. Date: Jan. 17, 2008

(65) Prior Publication Data
US 2009/0311757 A1    Dec. 17, 2009

(30) Foreign Application Priority Data

Jul. 13, 2006    (KR) .................. 10-2006-0065950

(51) Int. Cl.
*C12N 1/20*    (2006.01)
*C12P 13/10*    (2006.01)

(52) U.S. Cl. .............. 435/252.3; 435/114; 435/244
(58) Field of Classification Search .............. None
See application file for complete search history.

(56) References Cited

U.S. PATENT DOCUMENTS

| 3,849,250 A | 11/1974 | Nakayama et al. |
| 3,902,967 A | 9/1975 | Chibata et al. |
| 5,284,757 A | 2/1994 | Tsuchida et al. |
| 6,897,048 B2 | 5/2005 | Sakanyan et al. |
| 2005/0282258 A1 | 12/2005 | Jayaraman et al. |

FOREIGN PATENT DOCUMENTS

| EP | 0 378 223 A1 | 7/1990 |
| WO | WO-02/40643 A1 | 5/2002 |

OTHER PUBLICATIONS

T. Utagawa et al., "Production of Arginine by Fermentation", *J. Nutr.*, vol. 134 (10 Supp), pp. 2854S-2857S (2004).
H. Yoshida et al., "L Arginine Production by Arginine Analog-resistant Mutants of Microorganisms", *Agricultural and Biological Chemistry*, 45(4), pp. 959-963 (1981).

*Primary Examiner* — Irene Marx
(74) *Attorney, Agent, or Firm* — Peter F. Corless; Christine C. O'Day; Edwards Angell Palmer & Dodge LLP

(57) ABSTRACT

Disclosed herein are a microorganism producing L-arginine and a method of producing L-arginine using the same. The microorganism is a mutant strain of the genus *Corynebacterium*, *Corynebacterium glutamicum* CJR0500. The method for L-arginine production comprises activating the mutant strain *C. glutamicum* CJR0500 in a fermentation medium at 30° C. for 16 hours and then culturing the activated mutant strain for 72 hours with shaking.

3 Claims, No Drawings

METHOD FOR PRODUCING L-ARGININE USING *CORYNEBACTERIUM GLUTAMICUM*

TECHNICAL FIELD

The present invention relates to a microorganism producing L-arginine and a method of producing L-arginine using the microorganism. More particularly, the present invention relates to a mutant strain of the genus *Corynebacterium*, L-arginine-producing *Corynebacterium glutamicum* CJR0500, which has resistance to alpha-aminobutyric acid and the growth of which is stimulated by tryptophan, and a method of producing L-arginine using the mutant strain.

BACKGROUND ART

L-arginine, a semi-essential amino acid that is naturally produced in the body, has been widely used in medicaments, food, animal feedstuffs, and other products. L-arginine is useful as a drug for improving the hepatic function and brain function and treating male sterility, and as an ingredient of multiple amino acid supplements. Also, L-arginine has been used as a food additive in fish cakes and health beverages, and has recently gained interest as a salt substitute for hypertension patients.

Conventional methods for L-arginine production by biological fermentation are based on the production of L-arginine directly from carbon and nitrogen sources. For example, L-arginine can be produced using a mutant strain derived from a glutamic acid-producing microorganism belonging to the genus *Brevibacterium* or *Corynebacterium* (Japanese Pat. Laid-Open Publication Nos. Sho57-163487, Sho60-83593 and Sho62-265988), or using an amino acid-producing microorganism the growth properties of which are improved through cell fusion (Japanese Pat. Laid-Open Publication No. Sho59-158185). Also, L-arginine can be produced using a strain transformed with a recombinant gene (Japanese Pat. Laid-Open Publication No. Sho63-79597 and U.S. Pat. No. 4,775,623).

DISCLOSURE OF INVENTION

Technical Problem

The present inventors conducted intensive and thorough research in order to obtain a strain producing L-arginine at higher yields than conventional strains using a glutamic acid-producing strain, expecting that the strengthening of the glutamine biosynthetic pathway improves arginine productivity. This expectation is based on the feature of the pathway whereby arginine biosynthesis requires one molecule of glutamic acid and one molecule of glutamine, and a strain having resistance to alpha-aminobutyric acid, ananalogue of the amino acid isoleucine, increases glutamine productivity (Korean Pat. Laid-Open Publication No. 2002-0038204). Thus, the present inventors induced a mutant strain resistant to alpha-aminobutyric acid, canavanine and arginine hydroxamate from a parent strain, *Corynebacterium glutamicum* KFCC-10680, which produces glutamic acid and is resistant to sulphaguanidine and O-diazoleacetyl-L-serine (Korean Pat. Publication No. 91-7818). The mutant strain was found to produce L-arginine in higher yields than the parent strain, which is non-resistant to alpha-aminobutyric acid, thereby leading to the present invention.

Technical Solution

It is therefore an object of the present invention to provide a *Corynebacterium glutamicum* mutant strain CJR0500, which produces L-arginine and is resistant to alpha-aminobutyric acid, canavanine and arginine hydroxamate.

It is another object of the present invention to provide a method of producing L-arginine comprising activating the mutant strain in a fermentation medium and then culturing the mutant strain with shaking.

It is a further object of the present invention to provide a mutant strain CJR0500, which has a shorter arginine fermentation time in the presence of L-tryptophan.

Best Mode for Carrying Out the Invention

In one aspect, the present invention relates to a *Corynebacterium glutamicum* mutant strain CJR0500, which produce L-arginine and is resistant to alpha-aminobutyric acid, canavanine and arginine hydroxamate.

The mutant strain was induced as follows. The parent strain, *Corynebacterium glutamicum* KFCC-10680, which is resistant to sulphaguanidine and O-diazoleacetyl-L-serine, was treated with N-methyl-N-nitro-N-nitrosoguanidine (NTG), as a general method for mutagenesis, and smeared onto a minimal medium (see, Note 1) supplemented with alpha-aminobutyric acid, canavanine and arginine hydroxamate. Then, a mutant strain having resistance to the three compounds at 500 mg/L, 500 mg/L and 10 g/L, respectively, was selected.

The induction of the mutant strain will be described in more detail, as follows. The parent strain was activated through culturing in an activation medium (Note 2) for 16 hours. The activated strain was cultured in a seed medium (Note 3), which was sterilized at 121° C. for 5 minutes, for 14 hours. 5 ml of the seed culture were washed with 100 mM citric buffer, treated with 200 mg/L of NTG for 20 minutes, and washed with 100 mM phosphate buffer. The NTG-treated strain was then smeared onto the minimal medium (Note 1), and the viability thereof was evaluated. The strain was observed to have a death rate of 85%. In order to obtain a mutant strain resistant to all of alpha-aminobutyric acid, canavanine and arginine hydroxamate, the NTG-treated strain was smeared onto the minimal medium supplemented with canavanine, arginine hydroxamate and alpha-aminobutyric acid at 500 mg/L, 500 mg/L and 10 g/L, respectively, and cultured at 30° C. for 5 days. The emerged colonies were cultured in an Erlenmeyer flask containing an arginine production medium (Note 4) for 72 hours. A mutant strain, which produces arginine and is resistant to canavanine, arginine hydroxamate and alpha-aminobutyric acid, was selected and designated as *Corynebacterium glutamicum* CJR0500.

The present applicant deposited the mutant strain, *Corynebacterium glutamicum* CJR0500, at the Korean Culture Center of Microorganisms (KCCM), having an address at 361-221, Yurim B/D, Hongje-1-dong, Seodaemun-gu, SEOUL 120-091, Republic of Korea, on Mar. 15, 2006 so as to make it available to those skilled in the art, and the deposit was assigned accession number KCCM-10741P.

In another aspect, the present invention relates to a method of producing L-arginine comprising activating the mutant strain through culturing in a fermentation medium at 30° C. for 16 hours and then culturing the activated strain with shaking for 72 hours. With this method, the productivity of L-arginine was further increased (Example 1).

In a further aspect, the present invention relates to a mutant strain CJR0500 that has a shorter arginine fermentation time in the presence of L-tryptophan.

The addition of L-tryptophan to the fermentation medium further shortens the fermentation time of arginine, thereby producing much higher levels of L-arginine during the same fermentation time than those when L-tryptophan is not added to the medium (Example 3).

The microorganism of the present invention has the following properties.

Note 1. Minimal medium: 1.0% glucose, 0.4% ammonium sulfate, 0.04% magnesium sulfate, 0.1% potassium phosphate monobasic, 0.1% urea, 0.0001% thiamin, 200 µg/L biotin, 2% agar, pH 7.0

Note 2. Activation medium: 1% meat extract, 1% polypeptone, 0.5% sodium chloride, 0.5% yeast extract, 2% agar, pH 7.2

Note. 3 Seed medium: 5% glucose, 1% bactopeptone, 0.25% sodium chloride, 1% yeast extract, 3 µg/L biotin, 0.4% urea, pH 7.0

Note 4. L-arginine production medium: 4.0% glucose, 3% ammonium sulfate, 0.3% urea, 0.1% potassium phosphate monobasic, 0.1% potassium phosphate dibasic, 0.025% magnesium sulfate heptahydrate, 2.0% CSL (corn steep liquor), 200 µg/L biotin, pH 7.2

The mutant strain, *Corynebacterium glutamicum* CJR0500, which has improved arginine productivity and is resistant to canavanine, arginine hydroxamate and alpha-aminobutyric acid through mutagenesis using NTG, has the following properties of resistance to canavanine, arginine hydroxamate and alpha-aminobutyric acid (Table 1).

TABLE 1

Comparison of resistance to canavanine, arginine hydroxamate and alpha-aminobutyric acid

| Strain | Canavanine (mg/L) | | | | Arginine hydroxamate (mg/L) | | | | Alpha-aminobutyric acid (g/L) | | | | |
|---|---|---|---|---|---|---|---|---|---|---|---|---|---|
| | 0 | 300 | 500 | 800 | 0 | 300 | 500 | 800 | 0 | 1 | 5 | 10 | 20 |
| KFCC-10659 | +++ | − | − | − | +++ | − | − | − | +++ | ++ | + | − | − |
| CJR0500 | +++ | +++ | ++ | − | +++ | +++ | ++ | − | +++ | +++ | +++ | ++ | − |

The growth rates of the mutant strain according to L-tryptophan concentrations in the minimal medium are given in Table 2, below. As shown in Table 2, the mutant strain *Corynebacterium glutamicum* CJR0500 was found to require L-tryptophan.

TABLE 2

Growth rates according to varying concentrations of tryptophan

| Strain | Tryptophan (mg/L) | | | | |
|---|---|---|---|---|---|
| | 0 | 25 | 50 | 75 | 100 |
| KFCC-10659 | +++ | +++ | +++ | +++ | +++ |
| CJR0500 | + | ++ | +++ | +++ | +++ |

Mode for the Invention

A better understanding of the present invention may be obtained through the following examples, which are set forth to illustrate, but are not to be construed as the limit of, the present invention.

EXAMPLE 1

Strains used: KFCC-10680 and CJR0500

Fermentation medium (the same composition as the medium of Note 4): 4.0% glucose, 3% ammonium sulfate, 0.3% urea, 0.1% potassium phosphate monobasic, 0.1% potassium phosphate dibasic, 0.025% magnesium sulfate heptahydrate, 2.0% CSL (corn steep liquor), 200 µg/L biotin, pH 7.2

Fermentation and results: 24 ml of the fermentation medium was aliquotted into a 250-ml shaking Erlenmeyer flask and sterilized at 121° C. for 15 min. Each strain was cultured in the seed medium (Note 3) at 30° C. for 16 hrs. The activated strain (1 ml) was then inoculated in the sterilized fermentation medium and cultured at 30° C. for 72 hrs with shaking. The fermentation fluid was evaluated for arginine productivity, and the results are given in Table 3, below.

TABLE 3

| | KFCC-10680 | CJR0500 |
|---|---|---|
| Arginine productivity | 0.9 g/L | 2.8 g/L |

EXAMPLE 2

Strains used: KFCC-10680 and CJR0500

Fermentation medium: 10.0% glucose, 4% ammonium sulfate, 0.3% urea, 0.1% potassium phosphate monobasic, 0.1% potassium phosphate dibasic, 0.025% magnesium sulfate heptahydrate, 2.0% CSL (corn steep liquor), 200 µg/L biotin, pH 7.2

Fermentation and results: 24 ml of the fermentation medium was aliquotted into a 250-ml shaken Erlenmeyer flask and sterilized at 121° C. for 15 min. Each strain was cultured in the seed medium (Note 3) at 30° C. for 16 hrs. The activated strain (1 ml) was then inoculated in the sterilized fermentation medium and cultured at 30° C. for 72 hrs with shaking. The fermentation fluid was evaluated for arginine productivity, and the results are given in Table 4, below. The mutant strain, having resistance to alpha-aminobutyric acid, was found to produce L-arginine in a higher yield than the parent strain, which is non-resistant to the compound.

TABLE 4

| | KFCC-10680 | CJR0500 |
|---|---|---|
| Arginine productivity | 1.0 g/L | 3.5 g/L |

EXAMPLE 3

Strains used: KFCC-10680 and CJR0500

Fermentation medium: 10.0% glucose, 4% ammonium sulfate, 0.3% urea, 0.1% potassium phosphate monobasic, 0.1% potassium phosphate dibasic, 0.025% magnesium sulfate heptahydrate, 2.0% CSL (corn steep liquor), 200 µg/L biotin, 50 mg/L tryptophan, pH 7.2

Fermentation and results: 24 ml of the fermentation medium was aliquotted into a 250-ml shaking Erlenmeyer flask and sterilized at 121° C. for 15 min. Each strain was cultured in the seed medium (Note 3) at 30° C. for 16 hrs. The activated strain (1 nil) was then inoculated in the sterilized fermentation medium and cultured at 30° C. for 64 hrs with shaking. The fermentation fluid was evaluated for arginine productivity, and the results are given in Table 5, below. The addition of tryptophan was found to stimulate the growth of the mutant strain CJR0500 and thus produce L-arginine at a higher yield in a shorter time.

TABLE 5

|  | KFCC-10680 | CJR0500 |
| --- | --- | --- |
| Arginine productivity | 0.8 g/L | 3.45 g/L |

As described hereinbefore, the mutant strain of *Corynebacterium glutamicum*, CJR0500, which has resistance to alpha-aminobutyric acid, has increased L-arginine productivity. Also, since the addition of tryptophan shortens the fermentation time of arginine and thus allows the production of L-arginine in higher yields during the same fermentation time, the mutant strain is very useful.

INDUSTRIAL APPLICABILITY

As described hereinbefore, the mutant strain of *Corynebacterium glutamicum*, CJR0500, which has resistance to alpha-aminobutyric acid, has increased L-arginine productivity. Also, since the addition of tryptophan shortens the fermentation time of arginine and thus allows the production of L-arginine in higher yields during the same fermentation time, the mutant strain is very useful.

The invention claimed is:

1. A *Corynebacterium glutamicum* mutant strain CJR0500 (accession number KCCM-10741P), which produces L-arginine and is resistant to alpha-aminobutyric acid, canavanine and arginine hydroxamate.

2. A method of producing L-arginine, comprising activating the *Corynebacterium glutamicum* mutant strain CJR0500 (accession number KCCM-10741P) according to claim 1 in a fermentation medium at 30° C. for 16 hours; culturing the mutant strain for 72 hours with shaking; and recovering L-arginine from the medium.

3. The *Corynebacterium glutamicum* mutant strain CJR0500 (accession number KCCM-10741P) according to claim 1, growth of which is stimulated by addition of L-tryptophan.

* * * * *